(12) United States Patent
Yamamoto et al.

(10) Patent No.: US 8,112,144 B2
(45) Date of Patent: Feb. 7, 2012

(54) APPARATUS FOR DETERMINING BRAIN ATROPHY, METHOD OF DETERMINING BRAIN ATROPHY AND PROGRAM FOR DETERMINING BRAIN ATROPHY

(75) Inventors: Seiji Yamamoto, Hamamatsu (JP);
Baigalmaa Tsagaan, Boston, MA (US);
Keiichi Abe, Toyota (JP)

(73) Assignees: National University Corporation Shizuoka University, Shizuoka (JP);
National University Corporation Hamamatsu University School of Medicine, Shizuoka (JP)

( * ) Notice: Subject to any disclaimer, the term of this patent is extended or adjusted under 35 U.S.C. 154(b) by 593 days.

(21) Appl. No.: 12/295,261

(22) PCT Filed: Mar. 29, 2007

(86) PCT No.: PCT/JP2007/056839
§ 371 (c)(1),
(2), (4) Date: Nov. 6, 2008

(87) PCT Pub. No.: WO2007/114238
PCT Pub. Date: Oct. 11, 2007

(65) Prior Publication Data
US 2009/0221901 A1    Sep. 3, 2009

(30) Foreign Application Priority Data
Mar. 30, 2006 (JP) ................. P2006-094442

(51) Int. Cl.
*A61B 5/05* (2006.01)
(52) U.S. Cl. ............. 600/410; 600/411; 600/416
(58) Field of Classification Search .......... None
See application file for complete search history.

(56) References Cited

U.S. PATENT DOCUMENTS 5,551,431 A * 9/1996 Wells, III et al. ......... 600/410
5,876,337 A * 3/1999 Tsuda ..................... 600/410
(Continued)

FOREIGN PATENT DOCUMENTS
JP   2002209867   7/2002
(Continued)

OTHER PUBLICATIONS

English translation of International Preliminary Report on Patentability, corresponding to International Application No. PCT/JP2007/056839, mailed Nov. 27, 2008.

(Continued)

*Primary Examiner* — Unsu Jung
(74) *Attorney, Agent, or Firm* — Greenlee Sullivan P.C.

(57) ABSTRACT

Since cerebral atrophy does not occur only in a specific cross-section and reaches the brain in its entirety or arises prominently in a specific lobe (for example temporal lobe), for the assessment of cerebral atrophy, not only atrophy assessment for the frontal lobe but also an assessment also including atrophy of the temporal lobe, the parietal lobe and the occipital lobe is more desirable. The intracranial volume, the volume of the grey matter and the volume of the white matter are respectively extracted, computed and converted into numbers by image processing from a plurality of MRI slice images and the like. Ratios of these values from the conversions into numbers are taken to calculate the ratio of the grey matter and the ratio of the white matter with respect to the entire brain. Through comparison of a multitude of measurement data obtained by this automated computation, and a case, an objective cerebral atrophy assessment is carried out.

10 Claims, 9 Drawing Sheets

U.S. PATENT DOCUMENTS

| | | | |
|---|---|---|---|
| 6,366,797 B1* | 4/2002 | Fisher et al. | 600/410 |
| 2003/0053667 A1* | 3/2003 | Paragios et al. | 382/128 |
| 2005/0244036 A1* | 11/2005 | Rusinek et al. | 382/120 |
| 2005/0283054 A1* | 12/2005 | Reiman | 600/300 |

FOREIGN PATENT DOCUMENTS

| | | |
|---|---|---|
| JP | 2004174218 | 6/2004 |
| JP | 2004174220 | 6/2004 |
| JP | 2004529713 | 9/2004 |
| WO | WO 2006/013883 | 2/2006 |

OTHER PUBLICATIONS

Zhang et al., "Segmentation of Brain MR Images Through a Hidden Markov Random Field Model and the Expectation-Maximization Algorithm," 2001, IEEE Transactions on Medical Imaging, vol. 20, No. 1, pp. 45-57.

International Search Report, Corresponding to International Application No. PCT/JP2007/056839, Completed Jun. 13, 2007.

Leemput et al. (2003) "A Unifying Framework for Partial Volume Segmentation of Brain MR Images," *IEEE Transactions on Medical Imaging*, vol. 22, No. 1, pp. 105-119.

Madokoro et al. (2004) "Segmentation of Head Magnetic Resonance Image Using Self-Mapping Characteristic," *The Institute of Electronics, Information and Communication Engineers*, D-II vol. J87-D-II, No. 1, pp. 117-125.

Takeda et al. (1988) "Prospective and Longitudinal Study of Progress Speed of Brain Atrophy During Aging," *Japanese Journal of Geriatrics*, vol. 25, No. 1, pp. 44-47.

Taki (2005) "Brain magnetic resonance imaging diagnosis and clinical use diagnosing "normal aging brain" based on brain magnetic resonance images," Gekkan Shin'iryo, vol. 32, No. 6, pp. 81-84.

Ueyama et al. (1998) "Enhancement of Fine Structure in Medical Image Using Wavelet Analysis," *Computer Aided Diagnosis Theses*, vol. 2, No. 2 99, pp. 1-7.

\* cited by examiner

US 8,112,144 B2

APPARATUS FOR DETERMINING BRAIN ATROPHY, METHOD OF DETERMINING BRAIN ATROPHY AND PROGRAM FOR DETERMINING BRAIN ATROPHY

CROSS-REFERENCE TO RELATED APPLICATIONS

This application is the U.S. National Stage of International Application No. PCT/JP2007/056839, filed Mar. 29, 2007, which claims the benefit of Japanese Patent Application JP P2006-094442, filed Mar. 30, 2006, both of which are hereby incorporated by reference to the extent not inconsistent with the disclosure herewith.

TECHNICAL FIELD

The present invention relates to a device, a method and a program for assessing the atrophy of a brain from a cross-sectional slice image of a brain.

BACKGROUND ART

Methods using indicators such as bicaudate index (Bicaudate Cerebroventricular Index (CVI)) exist for the determination of brain atrophy. The portions flanked by the caudate nuclei is referred to as the anterior horns of the lateral ventricles, and these methods assess atrophy based on the value of the ratio between the width of the portion where a line passing through the caudate heads (heads of the caudate nuclei) intersects the lateral ventricles and the width of the portion where a line passing through the caudate heads intersects the outer sides of the frontal lobe (width of the frontal lobe). When this ratio exceeds a given value (for instance 15%), the brain is determined to be in an atrophic state. There are other methods taking the ratio of other locations to assess cerebral atrophy.

FIG. 6 is a figure showing an example of prior art cerebral atrophy assessment method. FIG. 6 (a) shows the locations of measurements by the bifrontal index, and FIG. 6 (b) shows the locations of measurements by the bicaudate index.

In addition, for imaging of brain tissues, it has been shown that extraction could be carried out from nuclear magnetic resonance (MRI) images according to the characteristics of each tissue such as white matter and grey matter to carry out computation of the surface area of each tissue in the slice plane (refer to Patent References 1 and 2 and Non-patent References 1 to 3).

Patent Document 1: Japanese Unexamined Patent Application Publication No. 2004-174218
Patent Document 1: Japanese Unexamined Patent Application Publication No. 2004-174220
Non-Patent Document 1: The Institute of Electronics, Information and Communication Engineers, D-II Vol. J87-D-II no. 1 pp. 117 to 125, 2004
Non-Patent Document 2: IEEE Trans. On Medical Imaging, Vol. 22 No. 1 pp. 105 to 119, 2003
Non-Patent Document 3: Computer Aided Diagnosis Theses, Vol. 2 No. 2 99. 1 to 7, 1998 Image

DISCLOSURE OF THE INVENTION

Problem to be Solved by the Invention

In prior art assessment techniques for cerebral atrophy, assessment by the bicaudate index or the like is carried out from one MRI slice image. With these methods, there are individual differences in brain structure, errors in the location of the cross-section to be sliced, and errors when measuring sizes from the image, such that variations in the numerical values to be assessed become large. In addition, bicaudate index and the like were originally indicators of ventriculomegaly, such that discrimination between hydrocephalus (a pathology in which the volume of cerebrospinal fluid accumulated in the cerebral ventricle increases, and the symptoms sometimes resemble cerebral atrophy) and cerebral atrophy (this is not the cerebral ventricle enlarged but the brain parenchyma atrophied and consequently the cerebral ventricle enlarged) is impossible if this is used.

In addition, problematic are the points that the measurements are not automated and the cumbersomeness of manually measuring and calculating exists, and that, consequently, a large amount of data cannot be handled, which does not allow a database to be created. In addition, since the calculation is carried out only for one transverse section, the atrophy of only one lobe (mainly the frontal lobe) can be assessed.

Since cerebral atrophy does not occur only in a specific cross-section and reaches the brain in its entirety or arises in a specific lobe (for example temporal lobe), for the assessment of cerebral atrophy, not only atrophy assessment for the frontal lobe but an assessment also including atrophy of the temporal lobe, the parietal lobe and the occipital lobe is more desirable, and methods are sought to enable this.

The present invention was devised to resolve the above problematic points, and an object is to provide a cerebral atrophy assessment device, a cerebral atrophy assessment method and a cerebral atrophy assessment program allowing cerebral atrophy to be assessed more objectively and readily.

Means for Solving the Problem

In order to achieve the above objective, the cerebral atrophy assessment device according to the present invention is provided with acquisition means for acquiring a slice image of the head portion, volume calculation means for calculating a numerical value representing the volume of a tissue or a region in the head portion based on the intensities of the pixels constituting the slice image acquired by the acquisition means, assessment means for assessing cerebral atrophy in the head portion from the numerical value calculated by the volume calculation means on the basis of preset assessment criteria, and output means for outputting information indicating the assessment result according to the assessment means.

With the cerebral atrophy assessment device according to the present invention, a numerical value representing the volume of a tissue or a region in the head portion is calculated from the slice image of the acquired head portion based on the intensities of the pixels constituting the slice image, and cerebral atrophy is assessed from the numerical value and based on preset criteria. Consequently, according to the cerebral atrophy assessment device according to the present invention, objectively and readily assessing cerebral atrophy becomes possible through image processing and preset criteria.

Desirably, the acquisition means acquires a plurality of slice images and the volume calculation means calculates each numerical value based on a plurality of slice images. According to this constitution, the numerical value representing the above volume calculated for the purpose of assessing cerebral atrophy can be more accurate, and more accurately assessing cerebral atrophy becomes possible.

Desirably, the volume calculation means calculates numerical values representing the intracranial volume of the head portion, and a brain volume comprising at least one of a volume of grey matter and a volume of white matter of the head portion, and the assessment means calculates the value of a ratio between the numerical value representing the intracranial volume of the head portion and the numerical value representing the brain volume calculated by the volume calculation means and assesses cerebral atrophy from the value of the ratio. According to this constitution, suitably assessing cerebral atrophy becomes possible from the intracranial volume and at least one volume among the grey matter and the white matter.

Desirably, the volume calculation means separates the outer portion of the brain and the cerebral ventricle portion within the intracranial volume and calculates a numerical value representing the volume of cerebrospinal fluid of the region occupied by the cerebrospinal fluid, and the assessment means assesses the cerebral atrophy based also on the numerical value representing the volume of cerebrospinal fluid calculated by the volume calculation means. According to this constitution, more suitably assessing cerebral atrophy becomes possible by further taking into consideration the cerebrospinal fluid.

Desirably, the volume calculation means calculates a numerical value representing the brain volume comprising at least one of the volume of the grey matter and the volume of the white matter of the head portion, and based on the intensities of pixels constituting the slice image acquired by the acquisition means, calculates at least one shape among the grey matter and the white matter of the head portion and calculates a convex hull of the shape to calculate a numerical value representing a volume of the convex hull, and the assessment means calculates the value of the ratio between the numerical value representing the volume of the convex hull calculated by the volume calculation means and the numerical value representing the brain volume and assesses the cerebral atrophy from the value of the ratio. According to this constitution, suitably assessing cerebral atrophy becomes possible from at least one shape among the grey matter and the white matter.

Desirably, the volume calculation means, based on the intensities of pixels constituting the slice image, distinguishes, by way of an EM (Expectation-Maximization) algorithm, a tissue or a region of the head portion indicated by the pixels and calculates a numerical value representing the volume. According to this constitution, since the above numerical value representing the volume calculated for the purpose of assessment of cerebral atrophy can be more accurate, assessing cerebral atrophy becomes possible more accurately.

Desirably, the volume calculation means calculates, by way of the EM algorithm, the probability that the pixels indicate a tissue or a region of the head portion, and calculates a value representing the volume based on the calculated probability. According to this constitution, the above numerical value representing the volume calculated for the purpose of assessment of cerebral atrophy can be more accurate, such that assessing cerebral atrophy becomes possible more accurately.

Desirably, the slice image is a slice image obtained by MRI. According to this constitution, it is ensured that a slice image in which the intensities of the pixels are different for each tissue or region of the head portion can be acquired, ensuring that the present invention can be carried out.

Desirably, the slice image is an image of a cross-section in a plane that is parallel to a plane passing through the centers of the external acoustic meatuses and the centers of the eyes in the head portion. According to this constitution, a suitable slice image can be acquired, allowing the present invention to be carried out suitably.

In addition to the possibility of describing the present invention as an invention of cerebral atrophy assessment device as described above, it can also be described as an invention of cerebral atrophy assessment method and cerebral atrophy assessment program, as described below. This is only a difference in the category, and the inventions are substantially identical, delivering similar actions and effects.

That is to say, the cerebral atrophy assessment method of the present invention is a cerebral atrophy assessment method performed by an information processing device, comprising: an acquisition step of acquiring a slice image of a head portion; a volume calculation step of calculating a numerical value representing a volume of a tissue or a region in the head portion based on intensities of pixels constituting the slice image acquired in the acquisition step; an assessment step of assessing cerebral atrophy in the head portion from the numerical value calculated in the volume calculation step on the basis of preset assessment criteria; and an output step of outputting information indicating an assessment result in the assessment step.

That is to say, the cerebral atrophy assessment program of the present invention causes an information processing device to execute an acquisition function for acquiring a slice image of the head portion, a volume calculation function for calculating a numerical value representing the volume of the tissue or the region in the head portion based on the intensities of the pixels constituting the slice image acquired by the acquisition function, an assessment function for assessing cerebral atrophy in the head portion from the numerical value calculated by the volume calculation function on the basis of preset assessment criteria, and an output function for outputting information indicating the assessment result according to the assessment function.

Effects of the Invention

According to the present invention, objectively and readily assessing cerebral atrophy becomes possible by image processing and preset criteria.

EXPLANATION OF REFERENCE NUMERALS

1 NUCLEAR MAGNETIC RESONANCE IMAGING DEVICE (MRI)
2 SIGNAL PROCESSING CIRCUIT

3 DISPLAY UNIT
11 CEREBROSPINAL FLUID (CSF)
12 CEREBRAL VENTRICLE
13 GREY MATTER
14 CRANIAL BONE
15 WHITE MATTER
100 CEREBRAL ATROPHY ASSESSMENT DEVICE
200 NUCLEAR MAGNETIC RESONANCE IMAGING DEVICE
300 PC
301 INPUT UNIT
302 VOLUME CALCULATION UNIT
303 ASSESSMENT UNIT
304 OUTPUT UNIT
400 RECORDING MEDIUM
400a PROGRAM STORAGE REGION
401 CEREBRAL ATROPHY ASSESSMENT PROGRAM
401a MAIN MODULE
401b INPUT MODULE
401c VOLUME CALCULATION MODULE
401d ASSESSMENT MODULE
401e OUTPUT MODULE.

BEST MODE FOR CARRYING OUT THE INVENTION

Hereafter, along with the figures desirable embodiments of cerebral atrophy assessment device, cerebral atrophy assessment method and cerebral atrophy assessment program according to the present invention will be describe in detail. Note that, in the description of the figures like elements are given like keys, and redundant descriptions are omitted. In addition, size ratios in the figures do not necessarily match those in the description.

Figure 7:
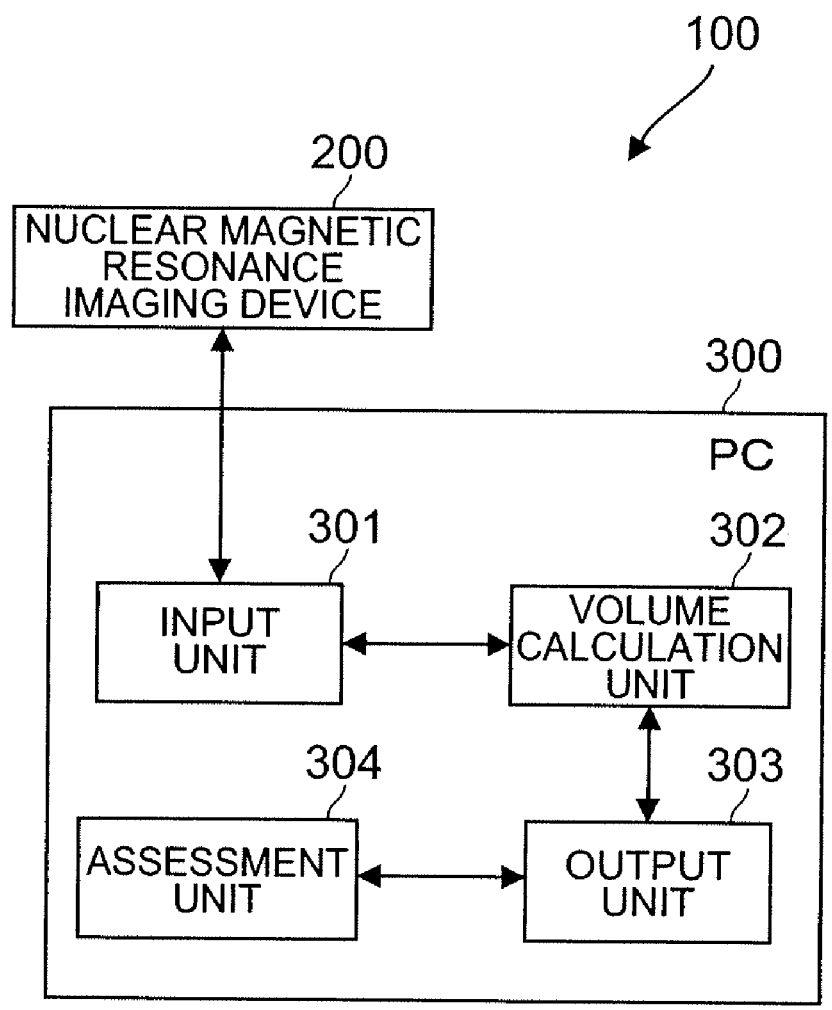
FIG. 7 Figure showing the constitution of a cerebral atrophy assessment device according to an embodiment of the present invention.

A cerebral atrophy assessment device 100 according to an embodiment of the present invention is shown schematically in FIG. 7. The cerebral atrophy assessment device 100 is a device for assessing atrophy of a brain from the slice image of a brain. As shown in FIG. 7, the cerebral atrophy assessment device 100 comprises a nuclear magnetic resonance imaging (MRI) device 200 and a PC (Personal Computer) 300.

The nuclear magnetic resonance imaging device 200 is an acquisition means for acquiring a slice image of the head portion of a subject of cerebral atrophy assessment. The nuclear magnetic resonance imaging device 200 uses nuclear magnetic resonance phenomenon to image in vivo information (in vivo imaging), and acquires a slice image. A slice image is an image showing interior of a head portion at a given cross-section. A pixel constituting a slice image has an intensity (pixel value) that corresponds to the tissue or the region in the head portion at a position corresponding to the pixel. The nuclear magnetic resonance imaging device 200 is coupled to a PC 300, and send the acquired data of the slice image of the head portion to PC 300.

Figure 3:
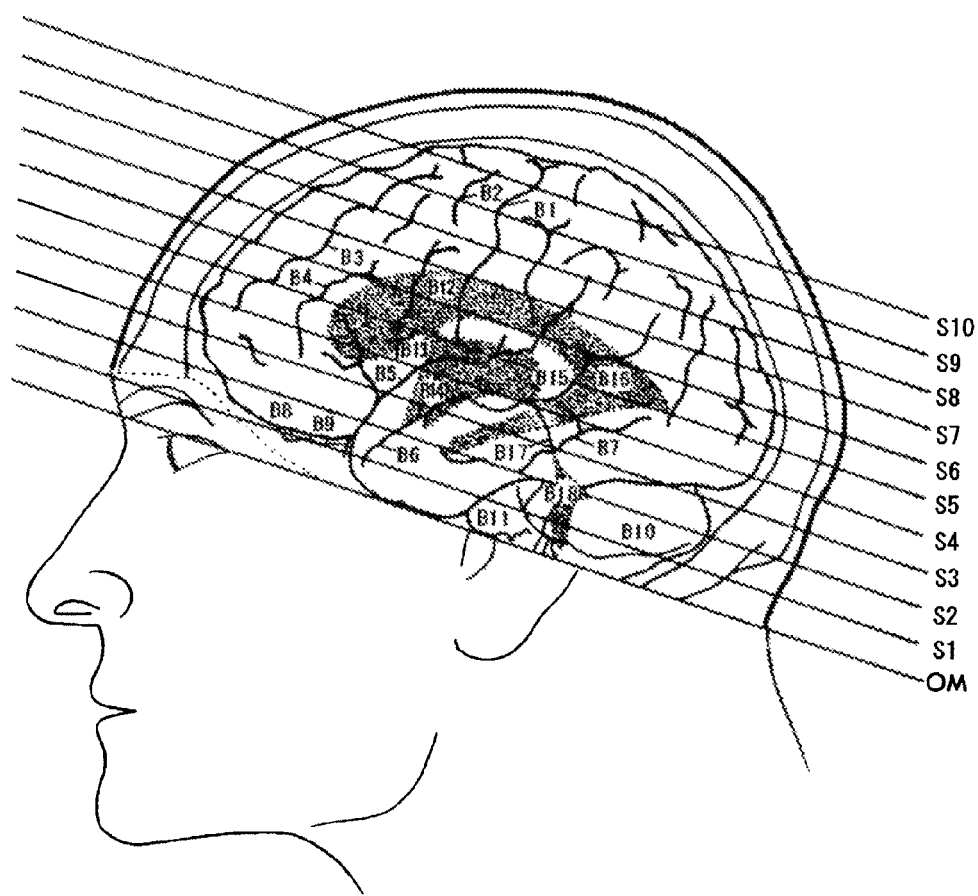
FIG. 3 Figure showing each site in the brain obtained when scanning parallelly to the OM line.

In addition, it is desirable that the slice image is an image having as a cross-section, a plane that is parallel to the plane passing through the centers of the external acoustic meatuses and the centers of the eyes in the head portion. A plane OM passing through the centers of the external acoustic meatuses and the centers of the eyes, and planes S1 to S10 parallel thereto are shown in FIG. 3. The planes S1 to S10 parallel to the plane OM passing through the centers of the external acoustic meatuses and the centers of the eyes, serving as cross-sections of the slice images, are located more on the parietal side than the plane OM. As described above, it is desirable that the nuclear magnetic resonance imaging device 200 acquires a plurality of slice images. Note that, it is desirable that the plurality of slice images are acquired with an interval of few mm units in a perpendicular direction to the cross-section. If the number of slice images increases, the definition in the vertical direction increases, such that a more suitable assessment of cerebral atrophy becomes possible. However, as the burden on the subject increases when the number of slice images to acquire increases, it is adequate to determine the number of slice images by also taking this point into consideration. In addition, there is no absolute necessity to acquire a plurality of slice images; one slice image may be acquired.

Figure 4:
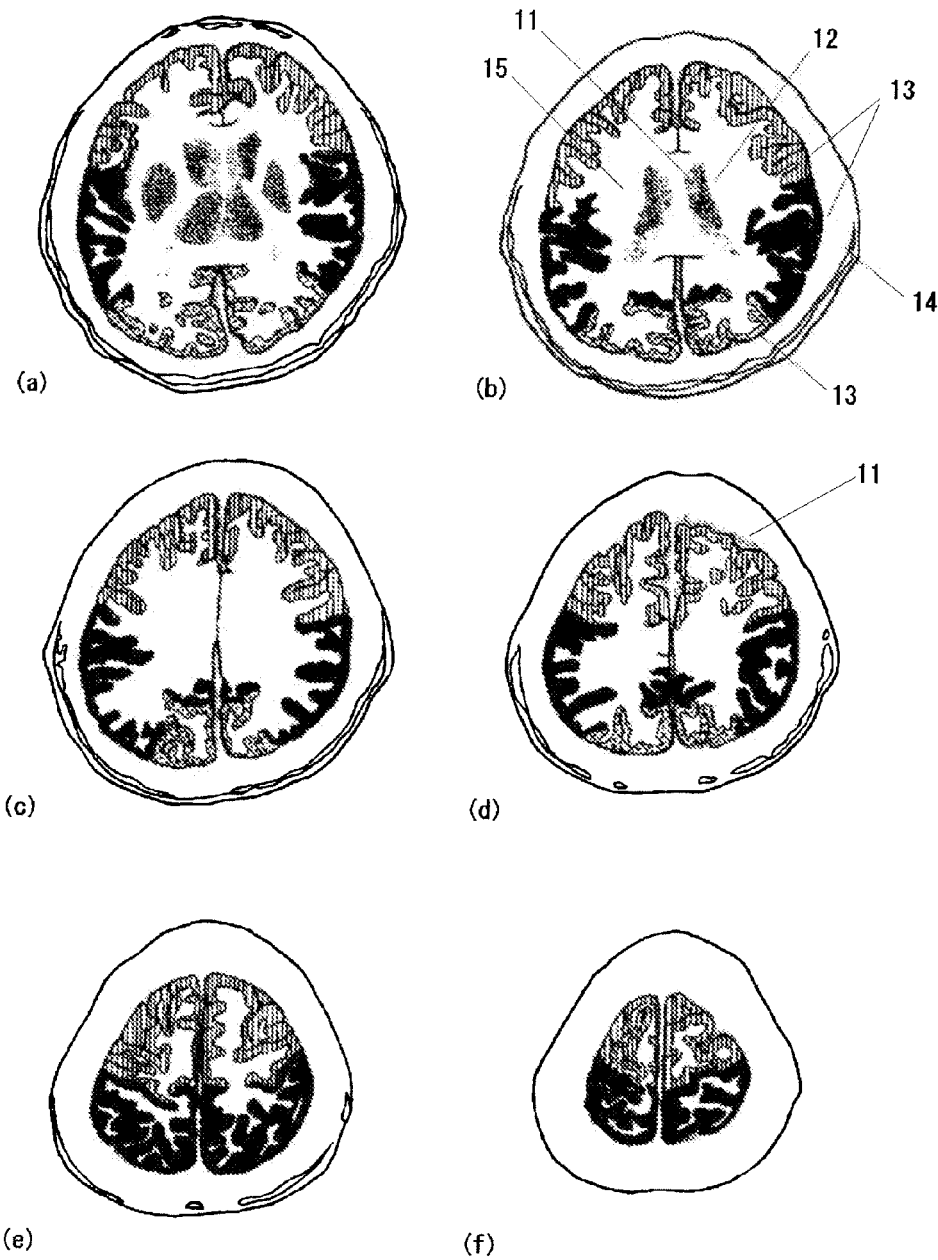
FIG. 4 Cross-sectional view of the brain scanned parallelly to the OM line.

Slice images of the head portion obtained by the nuclear magnetic resonance imaging device 200 are shown schematically in FIG. 4. FIG. 4 (a) is an image according to S5, FIG. 4 (b) is an image according to S6, FIG. 4 (c) is an image according to S7, FIG. 4 (d) is an image according to S8, FIG. 4 (e) is an image according to S9, and FIG. 4 (f) is an image according to S10. The black portions and the vertically hatched portions in the periphery are grey matter 13, and the white portions in the interior thereof are white matter 15. A cranial bone 14 is present on the outer side of the grey matter; however, in some places, cerebrospinal fluid 11 cavities are present between the cranial bone and the grey matter. In addition, a cerebral ventricle 12 is filled with cerebrospinal fluid 11.

Note that, as long as a slice image of the head portion having such pixels as described above is acquired, the cerebral atrophy assessment device 100 may use devices other than nuclear magnetic resonance imaging device 200, which are capable of acquiring such images. For instance, when the above a slice image can be acquired with a CT (Computed Tomography) device or a PET (Positron Emission Tomography) device, these devices may be used.

PC 300 is an information processing device that receives data of slice image acquired by the nuclear magnetic resonance imaging device 200 and carries out information processing. Concretely, PC 300 is constituted by hardware such as a CPU (Central Processing Unit) and memory, the functions of PC 300 described below are realized when these information processing devices run. As shown in FIG. 7, PC300 is provided with an input unit 301, a volume calculation unit 302, an assessment unit 303 and an output unit 304 as functionally constitutive elements.

The input unit 301 is means for receiving and entering data of a slice image of the head portion sent from the nuclear magnetic resonance imaging device 200. The input unit 301 delivers the received and entered data of the slice image to the volume calculation unit 302. Note that, in the cerebral atrophy assessment device 100, it not absolutely necessary to provide a nuclear magnetic resonance imaging device 200 per se as acquisition means for acquiring a slice image of the head portion as in the present embodiment, as long as a slice image of the head portion (imaged or the like by a nuclear magnetic resonance imaging device not included in the cerebral atrophy assessment device 100) is received by the input unit 301 (in this case, the input unit 301 becomes the acquisition means).

The volume calculation unit 302 is a volume calculation means for calculating a numerical value representing the volume of a given tissue or region in the head portion based on the intensities of the pixels constituting the slice image entered from the input unit 301. The tissue or region according to the calculated numerical value representing the volume, are appropriate for the content of cerebral atrophy assessment. Concretely, for instance, numerical values indicating the intracranial volume, which is the volume inside the cranial bone, as well as the brain volume, which is either or both of the volume of the grey matter and the volume of the white matter of the brain in the head portion are calculated. Also, in addition thereto, by separating the outer portion of the brain and the cerebral ventricle portion within the intracranial volume, a numerical value representing the volume of cerebrospinal fluid of the region occupied by the cerebrospinal fluid may be calculated. The volume of which tissue or region is to be calculated is preset in the volume calculation unit 302 according to the content of the cerebral atrophy assessment.

As described above, representation is made with the intensities of the pixels that correspond to these tissues or regions on the slice image. That is to say, the volume calculation unit 302 extracts the pixels having the intensities corresponding to each tissue or region to distinguish each tissue or region, allowing the tissue or the region to be recognized. The volume calculation unit 302 calculates a numerical value representing a volume based on each tissue or region recognized in the slice image. Concretely, for instance, regarding the intracranial volume, the shape of cranial bone can be recognized and the surface area in the inner region thereof be calculated as the above numerical value. In addition, regarding the grey matter and the white matter, the surface area of the shape thereof per se can be calculated as the above numerical value. Further, if there is a plurality of slice images, the numerical value representing volume can be calculated by taking the total sum of the numerical values obtained from each slice image. In this case, the total sum may be taken by multiplying the surface area by a distance between the plurality of slice images (interval).

The above process of extracting pixels having intensities that correspond to each tissue or region to distinguish each tissue or region can be carried out concretely by way of an EM algorithm. Information indicating the mean value and the dispersion of the intensity values of the pixels of each tissue or region is memorized beforehand by the volume calculation unit 302, and the above process is carried out based on this information by the EM algorithm. Note that, in so doing, it is hypothesized that the distribution of the intensities of the pixels corresponding to each tissue is a Gaussian distribution. In addition, it is desirable that, in so doing, the probability that a pixel constituting the slice image indicates any of the tissues or regions of the head portion is calculated by the EM algorithm and the calculated probabilities integrated, to calculate the above value representing the volume. This calculates, for instance, via the EM algorithm a ratio signifying that a pixel indicates 10% grey matter and 90% white matter, to calculate a volume from the ratios of all the pixels. This allows the partial volume effect between each of the tissues or regions to be taken into consideration, allowing for a more accurate calculation of volume.

Figure 5:
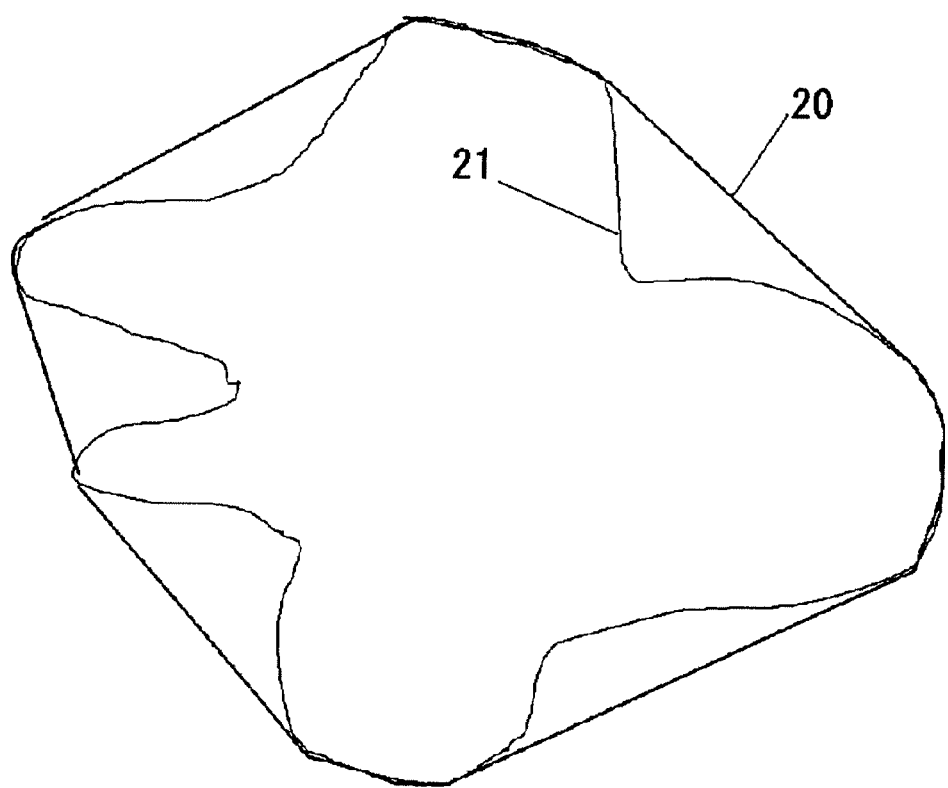
FIG. 5 Descriptive figure of convex hull.
Figure 6:
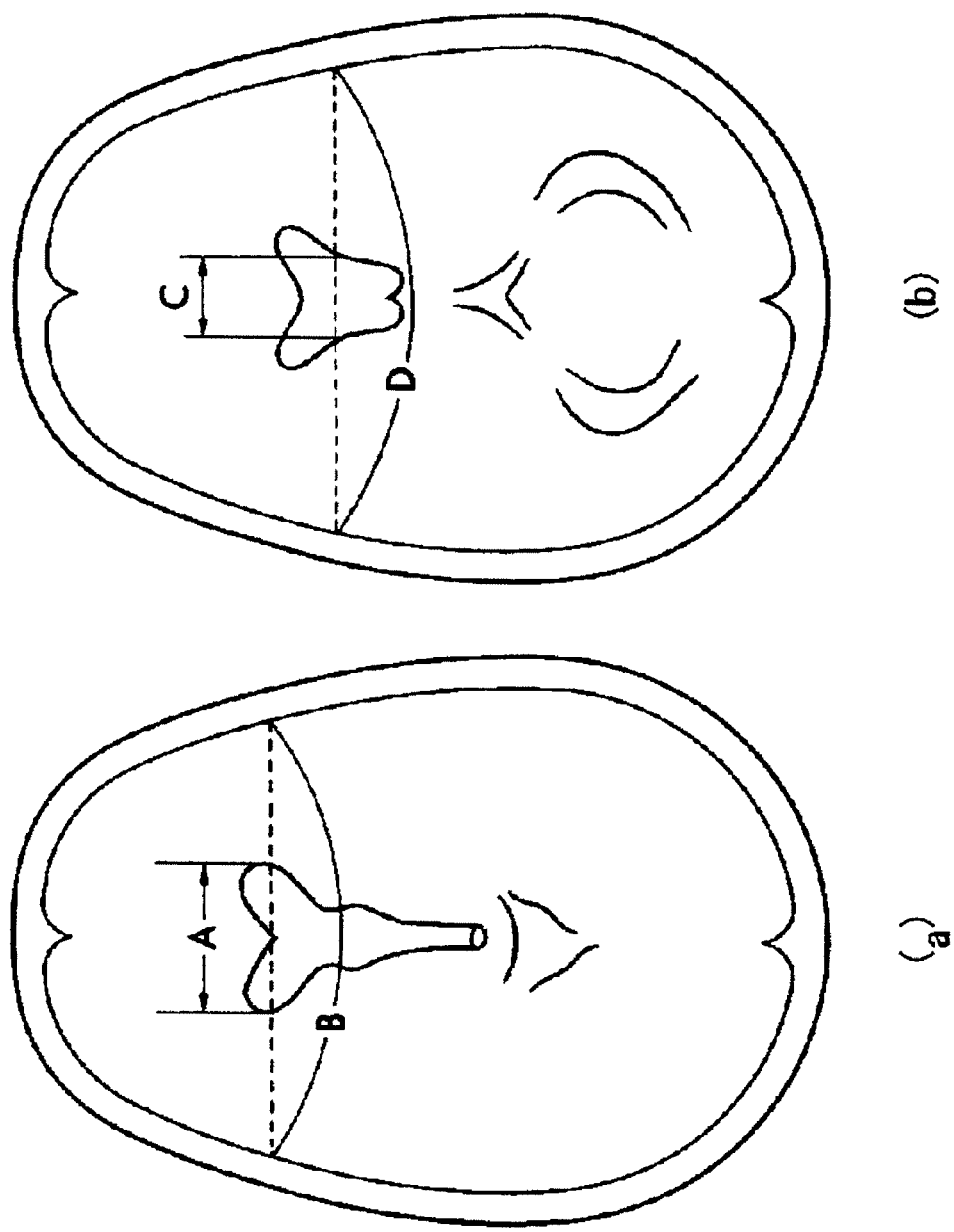
FIG. 6 Figure showing an example of prior art cerebral atrophy assessment method.

In addition, the volume calculation unit 302 calculates at least one shape from the grey matter and the white matter of the head portion according to the content of cerebral atrophy assessment and based on the intensities of the pixels constituting the slice images, calculates the convex hull of the shape and calculates a numerical value representing the volume of convex hull. The concept of a two-dimensional convex hull is shown in FIG. 5. A curve 20 on the outside indicates a convex hull and a curve 21 is a given diagram. A convex hull is a convex diagram that can internalize a given diagram with the minimum surface area. Calculations of the shapes of the grey matter and the white matter can be carried out by the EM algorithm, similarly to the method described above. In addition, existing methods can be applied to the calculation of the convex hull of a shape. The volume calculation unit 302 has memorized beforehand an algorithm memorized beforehand and a processing content, and carries out calculation of the above volume. The volume calculation unit 302 delivers each calculated numerical value representing a volume to the assessment unit 303.

The assessment unit 303 is an assessment means for assessing cerebral atrophy in the head portion, from the numerical value representing a volume calculated by the volume calculation unit 302 and based on preset criteria memorized in the assessment unit 303. This assessment includes the assessments of whether or not cerebral atrophy has occurred in the head portion, in addition, if cerebral atrophy has occurred, to which extent the degree of cerebral atrophy is. As criteria set in the assessment unit 303, concretely, for instance, there are those that use a value obtained by dividing the numerical value representing the brain volume, which is either or both of the volume of grey matter and the volume of white matter, by the numerical value representing the intracranial volume. That is to say, it is possible to calculate the value of the ratio between the numerical value representing the intracranial volume and the numerical value representing the brain volume and use the value for the assessment of cerebral atrophy. The above divided value per se may be used as a value representing the degree of cerebral atrophy, or, the assessment of whether or not there is cerebral atrophy may be according to whether or not the value is below a preset threshold value. Since either or both of the volume of the grey matter and the volume of white matter become smaller with respect to the intracranial volume if cerebral atrophy has occurred, the above criteria can be used, and suitably assessing cerebral atrophy becomes possible. In addition, since which one becomes smaller differs according to the type of cerebral atrophy, it is desirable to carry out assessment using the values of both the volume of grey matter and the volume of white matter.

Furthermore, a numerical value representing the volume of cerebrospinal fluid may be used for the assessment of cerebral atrophy. For instance, concretely, assessment of cerebral atrophy may be carry out using a value obtained by dividing the numerical value representing the volume of cerebrospinal fluid in the outer portion of the brain and the brain matter portion, or in either one thereof, by the numerical value representing the intracranial volume. The assessment using this value, similarly to the one described above, may use the value per se as the assessment result, or an assessment using a threshold value may also be carried out. Since each volume of cerebrospinal fluid described above may vary depending on the cerebral atrophy, the above criteria can be used, and more suitably assessing cerebral atrophy becomes possible.

In addition, the assessment unit 303 may carry out assessment of cerebral atrophy based on the numerical value representing the volume for at least one of the grey matter and the white matter, and the numerical value representing the volume of convex hull thereof. For instance, the assessment of cerebral atrophy can be carried out using a value obtained by dividing the numerical value representing the volume for at least one of the grey matter and the white matter with the numerical value representing the volume of convex hull thereof. Similarly to the criteria described above, the above divided value per se may be used as a value representing the degree of cerebral atrophy, or an assessment as to whether or not there is cerebral atrophy may be carried out according to whether or not the value is lower than a preset threshold value. Since the shape of either or both of the grey matter and the white matter sometimes distort if cerebral atrophy has occurred, the above criteria can be used, and suitably assessing cerebral atrophy becomes possible. In addition, since which one becomes distorted differs according to the type of cerebral atrophy, it is desirable to carry out the assessment using the values for both the volume of grey matter and the volume of white matter.

The assessment unit 303 delivers the information indicating the result of assessment of cerebral atrophy assessed as described above to the output unit 304.

Note that, regarding the numerical values representing volumes calculated by volume calculation unit 302, the numerical values calculated by the assessment unit 303 for the assessment of cerebral atrophy and the information indicating the result of assessment of cerebral atrophy by the assessment unit 303, storage in a database is desirable. In this way, using the information stored in the database, the threshold values described above can be determined by statistical treatment, and time series comparative examination of assessment results can be carried out.

The output unit 304 is an output means for delivering the information indicating the assessment result by the assessment unit 303. This delivery is carried out with respect to, for instance, a monitor (not shown) connected to PC 300. The monitor displays the information, which allows a user such as a physician to learn of the assessment result. The above was the constitution of the cerebral atrophy assessment device 100.

Figure 8:
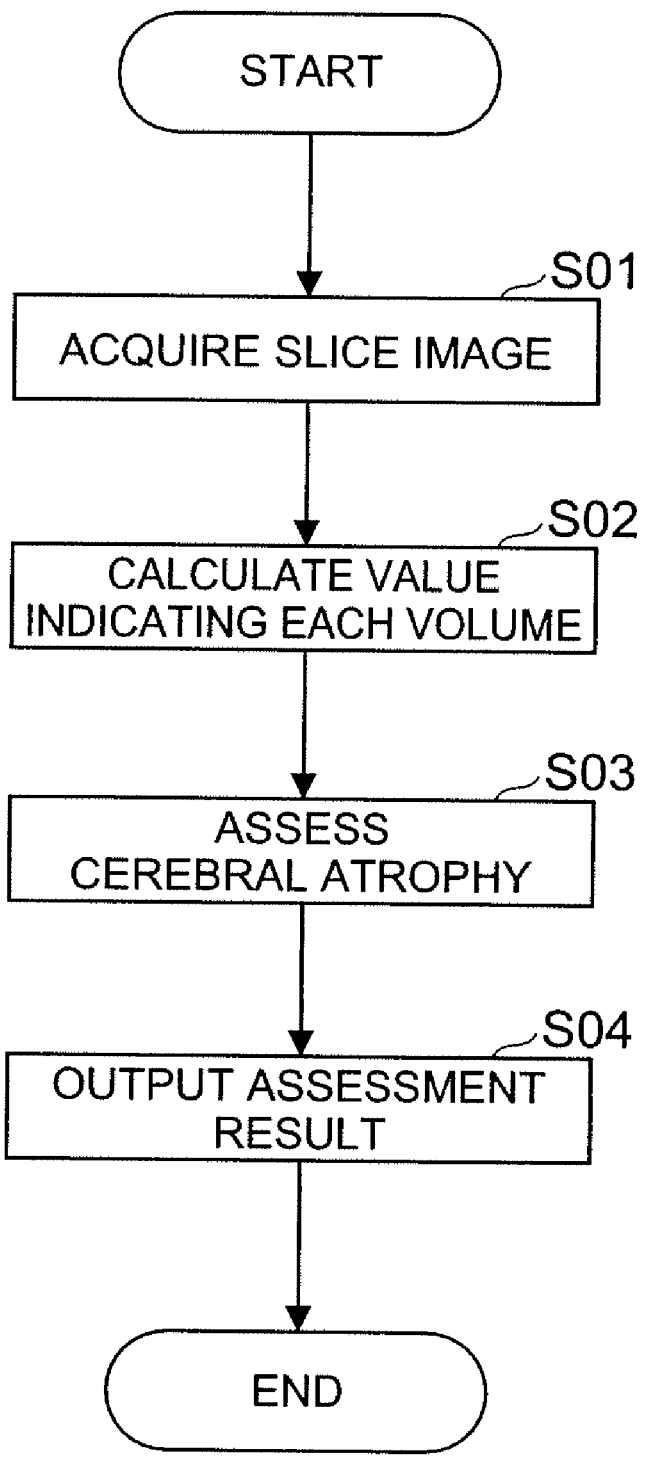
FIG. 8 Flow chart showing the processing with the cerebral atrophy assessment device (cerebral atrophy assessment method) according to an embodiment of the present invention.

Next, the operation of a cerebral atrophy assessment device 100 (cerebral atrophy assessment method) will be described referring to the flow chart of FIG. 8. In the cerebral atrophy assessment device 100, a slice image of the head portion is acquired by a nuclear magnetic resonance imaging device 200 (S01, acquisition step). The data of the acquired slice image is sent to PC 300. In PC 300, the data of the slice image is entered and delivered to a volume calculation unit 302 by an input unit 301.

Next, in PC 300, a numerical value representing the volume of a tissue or a region in the head portion needed for the assessment of cerebral atrophy from the slice image is calculated by the volume calculation unit 302 (S02, volume calculation step). The calculated numerical value is entered from the volume calculation unit 302 into an assessment unit 303. Next, from the numerical value calculated by volume calculation unit 302, cerebral atrophy is assessed by the assessment unit 303 (S03, assessment step). The information indicating the result of the assessment is delivered from the assessment unit 303 to an output unit 304. Next, as described above, the information indicating the result of the assessment is delivered to a monitor or the like by the output unit 304, and displayed by the monitor (S04, output step).

As described above, in the cerebral atrophy assessment device 100 according to the present embodiment, a numerical value representing the volume of a tissue or a region needed for assessing cerebral atrophy is calculated based on the intensities of the pixels constituting the acquired slice image of the head portion. In addition, cerebral atrophy is assessed by preset decision criteria. Consequently, according to the cerebral atrophy assessment device 100 according to the present embodiment, an objective assessment of cerebral atrophy becomes possible. In addition, since calculation of numerical values by information processing and assessment of cerebral atrophy based thereupon are carried out, an objective assessment becomes possible.

In addition, as described above, by using a plurality of slice images to evaluate the numerical values representing the volumes of each tissue or region three-dimensionally in the entirety of the brain including the frontal lobe, the temporal lobe, the parietal lobe and the occipital lobe, the numerical values representing the volumes can become more accurate, and more accurately assessing cerebral atrophy becomes possible.

In addition, by using the EM algorithm for the calculation of volume, the above numerical values representing the volumes calculated for the assessment of cerebral atrophy can become more accurate, and more accurately assessing cerebral atrophy becomes possible.

In addition, using images obtained by MRI as the slice images ensures that a slice image in which the intensity of a pixel is different for each tissue or region in the head portion can be acquired, ensuring that the present invention can be carried out. In addition, if the slice image is an image having as cross-section a plane that is parallel to the plane passing through the centers of external acoustic meatuses and the centers of the eyes in the head portion, a suitable slice image can be acquired, allowing the present invention to be carried out suitably.

Figure 9:
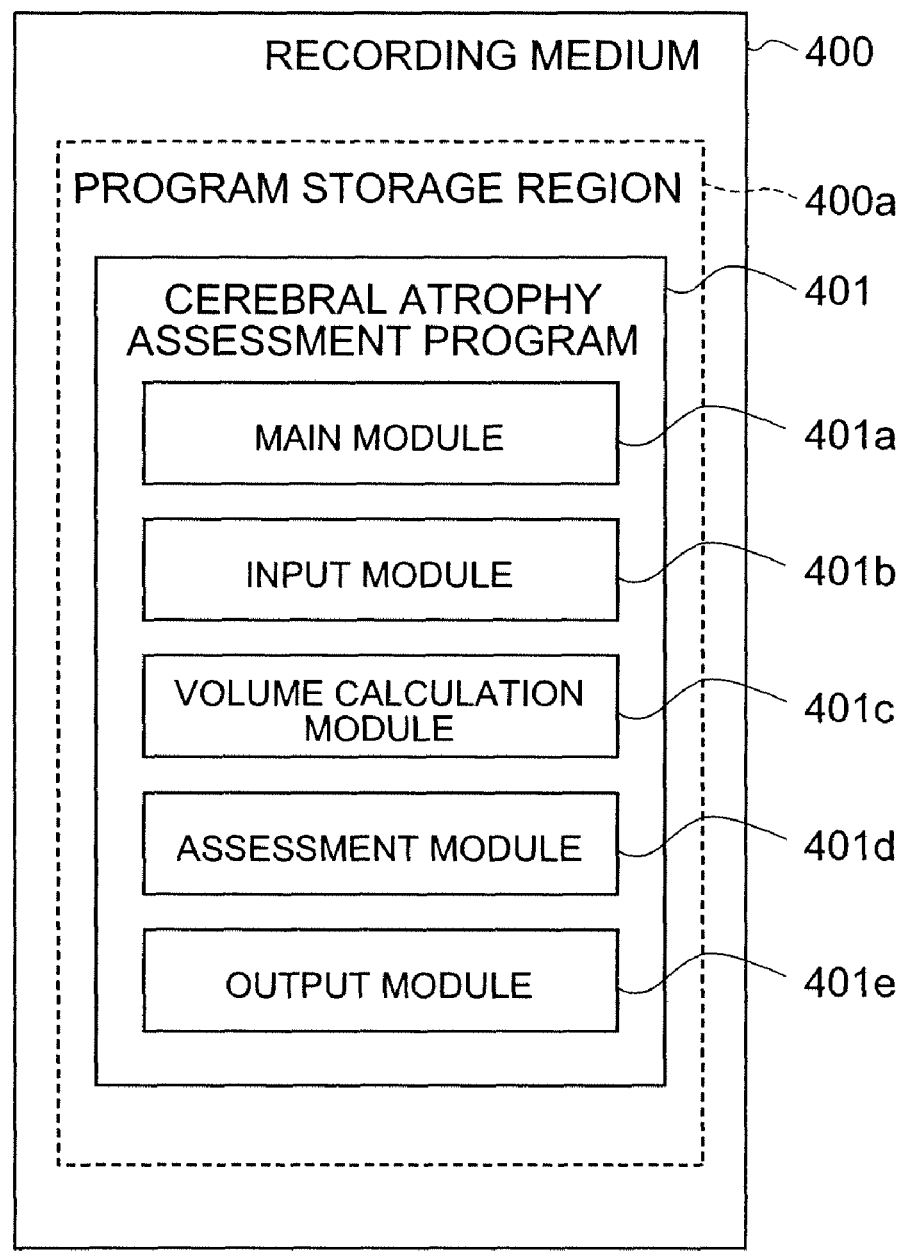
FIG. 9 Figure showing the constitution of the cerebral atrophy assessment program of the present invention.

Next, a cerebral atrophy assessment program for causing an information processing device to execute the process of carrying out the above series of assessments of cerebral atrophy will be described. As shown in FIG. 9, a cerebral atrophy assessment program 401 is stored inside a program storage region 400a formed on a recording medium 400 the information processing device is provided with.

The cerebral atrophy assessment program 401 is constituted by a main module 401a for controlling the process of cerebral atrophy assessment overall, an input module 401b, a volume calculation module 401c, an assessment module 401d and an output module 401e. The functions that are realized by executing the input module 401b, the volume calculation module 401c, the assessment module 401d and the output module 401e are respectively identical to the functions of the input unit 301, the volume calculation unit 302, the assessment unit 303 and the output unit 304 of the above PC 300.

Note that the cerebral atrophy assessment program 401 may have such a constitution that a portion or the entirety thereof is transmitted via a transmission medium such as a communication line and received by another instrument to be recorded (including installed).

The cerebral atrophy assessment device according to the present invention comprises means for obtaining a slice image of the brain, means for computing the volume of the grey matter and/or the volume of the white matter from a plurality of slice image similarly to means for computing intracranial volume from a plurality of obtained slice images, means for assessing cerebral atrophy from the value of the ratio between the previous intracranial volume and the volume of the grey matter and/or the value of the ratio between the previous intracranial volume and the volume of the white matter.

In addition, it is desirable that as for the cerebral atrophy assessment device, the previous means for computing the intracranial volume and the volume of the grey matter and/or the volume of the white matter has means for extracting each tissue from a plurality of slice images and means for integrating over the entirety of the slice images to compute a volume.

In addition, it is desirable that the previous slice image of a brain is a slice image obtained by MRI.

In addition, it is desirable to set the lower end of the slice images used for computation with the plane joining the centers of the external acoustic meatuses and the centers of the eyes as the reference.

In addition, in the previous means for extracting each tissue from the slice images, it is desirable to use EM algorithm as the extraction algorithm.

In addition, in the previous EM algorithm, it is desirable that the volume of the grey matter and/or the volume of the white matter is determined probabilistically by integrating the probability given to each voxel.

In addition, it is desirable to provide means for determining the volume of cerebrospinal fluid by separating the region occupied by the cerebrospinal fluid into the outer portion of the brain (between the dura matter and the grey matter) and the cerebral ventricle portion further within the intracranial volume.

In addition, the cerebral atrophy assessment device according to the present invention comprises means for obtaining a slice image of a brain, means for determining a two-dimensional (or three-dimensional) convex hull of the grey matter of the brain from a plurality of obtained slice images and/or means for determining a two-dimensional (or three-dimensional) convex hull of the white matter of the brain from a plurality of slice images, and means for assessing cerebral atrophy from the value of the ratio between the previous volume of convex hull and volume of the grey matter and/or the value of the ratio between the previous volume of convex hull and volume of the white matter.

For the assessment of cerebral atrophy, the present invention extracts, computes and converts into numbers the intracranial volume (region containing the brain parenchyma comprising the grey matter and the white matter, and the cerebrospinal fluid), the volume of the grey matter and the volume of the white matter, respectively, by image processing from a plurality of MRI slice images and the like. The present invention takes the ratio of these values from the conversions into numbers to calculate the ratio of the grey matter and the ratio of the white matter with respect to the intracranial volume. The invention provides a device capable of objectively assessing cerebral atrophy through comparison of a multitude of measurement data obtained by this automated computation, and a case.

According to the above constitution, since the extent of the atrophy is converted into a number to be assessed, by taking the ratio between the intracranial volume of the brain in its entirety including the frontal lobe, the temporal lobe, the parietal lobe, and the occipital lobe, and the volume of the grey matter and/or the volume of the white matter, which carry out the function of the brain, there are little variations, setting the criteria is straightforward, assessment is accurate and becomes stable, with respect to prior art conversion into a number only with mainly the frontal lobe in one slice plane.

In addition, according to the above constitution:

Since the intracranial volume, the volume of the grey matter and the volume of the white matter are computed from surface areas of the slice image, improving the accuracy of volume measurements is straightforward by increasing the number of slices.

Each tissue characteristic is readily seen on the images by using MRI images, improving the precision of the separation of tissue regions.

Since the lower end of the brain has a complex structure, extracting the brain region accurately is difficult. Thus, a reference plane that can be automatically extracted from MRI is set and only slice images that are above this are used to compute the intracranial volume, the volume of the grey matter and the volume of the white matter. As the reference plane, for instance, specification such as, the plane that joins the centers of the external acoustic meatuses and the centers of the eyes, or how many mm above this plane can be considered. Even if the ratio between the intracranial volume and the volume of the grey matter or the volume of the white matter is determined by ignoring the lower part of the brain in this way, no problem occurs since all the portions involved considerably in conditions due to cerebral atrophy such as dementia.

By extracting each tissue region using the EM algorithm, the accuracy of region assessment rises thereby raising the accuracy of calculation of the surface area, thus, the accuracy of volume calculation is improved. As a result, the stability of cerebral atrophy assessment is improved.

Based on the results of the EM algorithm, by determining the integration of the volume of the grey matter and the volume of the white matter, not by classifying deterministically each voxel (unit cube or rectangular parallelepiped serving as the basis for computation) into a tissue, but by considering the probability of belonging to each obtained tissue, the volume of the grey matter and the volume of the white matter can be sought with higher accuracy.

Since data are collected automatically, by converting these into a database, comparative examination is possible among many cases or in a time series of an identical individual, which increases the accuracy of cerebral atrophy assessment.

The dura matter, the white matter, the grey matter, the cerebrospinal fluid (CSF) and the PV (Partial Volume: voxel where a plurality of tissue co-exist) regions are classified and extracted from the MRI image of the brain through the EM (Expectation-Maximization) algorithm.

From these, an intracranial ventricle surface area, a grey matter region surface area, a white matter region surface area and a cerebrospinal fluid surface area are calculated.

These are applied to the entirety of slice images to calculate an intracranial volume, a volume of the grey matter, a volume of the white matter and a volume of cerebrospinal fluid.

Figure 1:
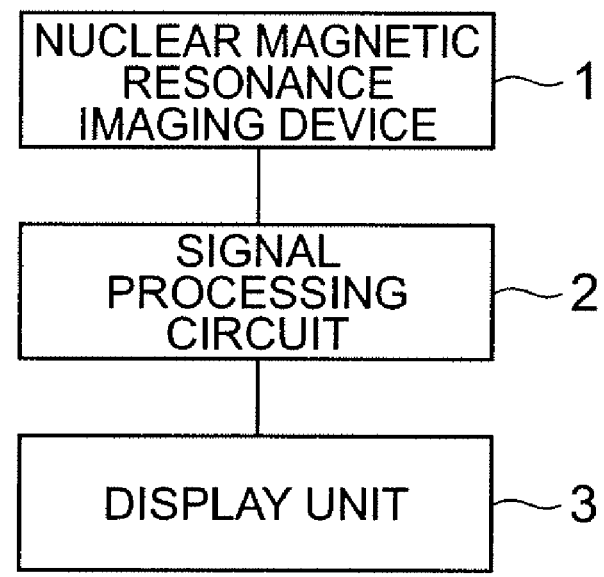
FIG. 1 Overview of cerebral atrophy assessment device.

An overview of the cerebral atrophy assessment device is shown in FIG. 1. Reference numeral 1 is a nuclear magnetic resonance imaging device (MRI), reference numeral 2 is a signal processing circuit, and numeral 3 is a display unit.

Figure 2:
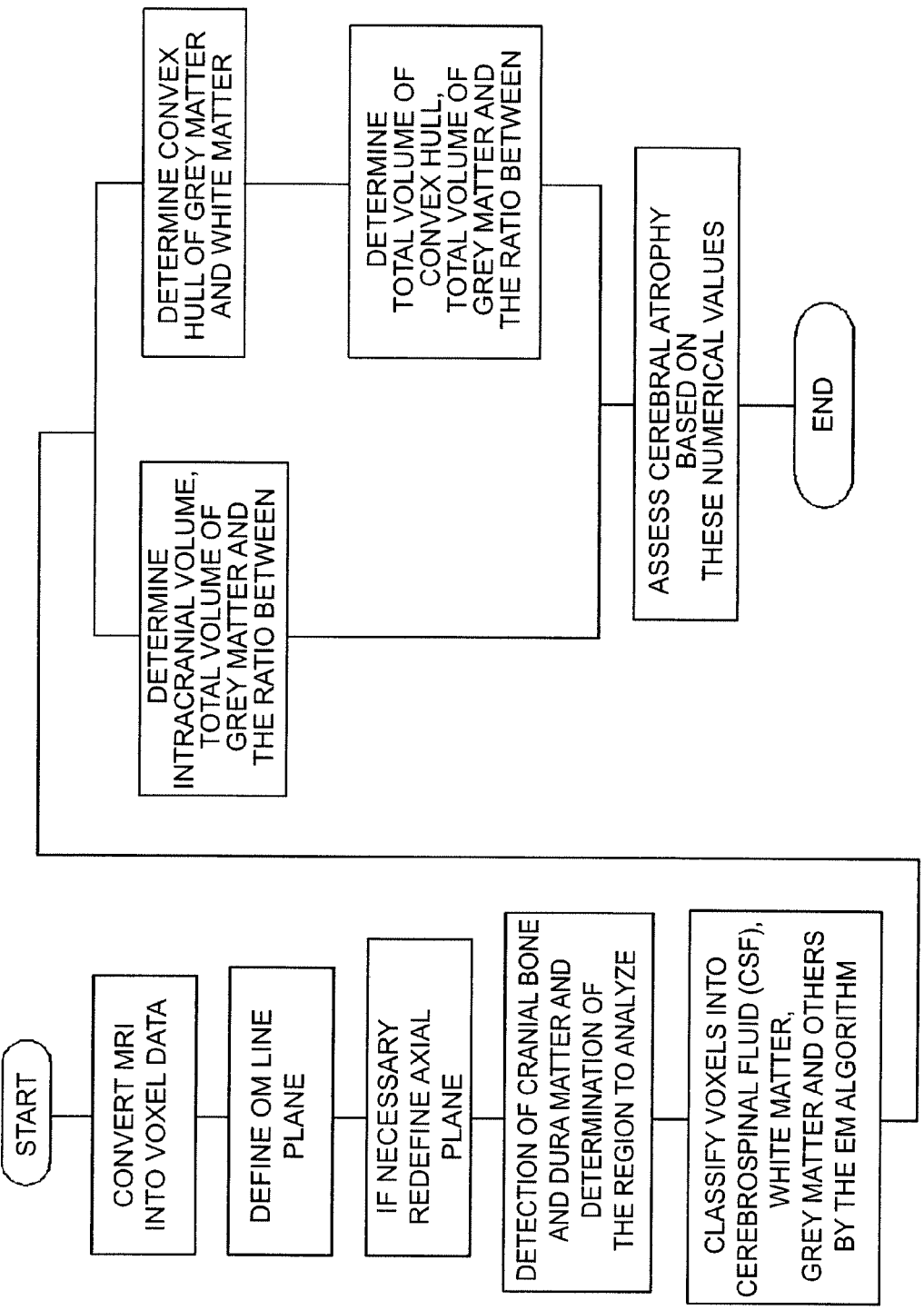
FIG. 2 Overall flow chart of cerebral atrophy assessment method.

In the signal processing circuit 2, each step from the following is executed sequentially (FIG. 2).

1. An imaged MRI normally has different intra-slice definition and inter-slice definition (slice thickness and slice interval). This may be used as a rectangular parallelepiped voxel centered on each point as-is, or may be converted into cubic voxel data by interpolation or the like and used.

2. Although the actual OM line plane is a plane passing through the centers of the external acoustic pores and the centers of the eye pits, since these are difficult to identify on the MRI, the centers of the left and right external acoustic meatuses and the centers of both eyes are detected, and the plane containing these serves as an approximate OM line plane.

3. If the angle formed by the OM line plane and the axial cross-section is greater than a given extent, axial cross-section is re-defined so as to become parallel to the OM line plane.

4. The cranial bone and the dura matter is detected, and the range comprising the interior and the bottom portions thereof limited by the OM line plane (or a slice cross-section above from there by a defined length) serves as the region subjected to analysis (a portion of the intracranial region).

5. The EM algorithm is applied to the density distribution of voxels in this analysis subject region, which are classified into a cerebrospinal fluid (CSF), a grey matter, a white matter and other regions. In so doing, the Partial Volume effects between the CSF and the grey matter, and between the grey matter and the white matter are taken into consideration, initial distributions in regard to these are also prepared. It is also conceivable that physicians and others specify the learning region in regard to the CSF, the grey matter and the white matter respectively.

6a. The number of voxels in the region defined in 4 serving as the intracranial volume subjected to consideration, and the number of voxels in the region classified as the grey matter in 5 serving as the volume of the grey matter, the volume of the white matter and the volume of the cerebrospinal fluid, the ratio thereof with respect to the intracranial volume serve as an index indicating the extent of cerebral atrophy.

6b. With respect to the region integrating the grey matter and the white matter defined in 5, a two-dimensional convex hull is determined for each slice cross-section, or a three-dimensional convex hull is determined directly; the number of voxels inside the convex hull serving as the volume of the convex hull and the number of voxels in the region classified as grey matter in 5 serving as the volume of the grey matter, the ratio between these serve as an index indicating the extent of cerebral atrophy.

Each site of the brain obtained when scanning parallelly to the OM line is shown in FIG. 3. B1 is a central sulcus, B2 is a pre-central sulcus, B3 is a superior frontal sulcus, B4 is an inferior frontal sulcus, B5 is a lateral sulcus (Sylvius fissure), B6 is a superior temporal sulcus, B7 is an inferior temporal sulcus, B8 is an olfactory bulb, B9 is an olfactory bundle, B10 is the cerebellum, B11 is a bridge, B12 is a lateral ventricle, B13 is an interventricular foramina (foramina of Monroe), B14 is the third ventricle, B15 is the suprapineal recess, B16 is a trigone of cerebral ventricle, B17 is the aqueduct of the mid brain and B18 is the fourth ventricle. This is taken as a plane containing the OM line, that is to say, a line passing through the centers of the external acoustic pores and the centers of the eye pits serving as the reference plane, images at a plurality of slice planes parallel to this reference plane are obtained by MRI. Note that, since the centers of the external acoustic pores and the centers of the eye pits are difficult to identify at the time of actual MRI imaging, imaging is carried out with the line joining the corners of the eyes to the centers of the external acoustic pores serving as the OM line. Furthermore, when determining the OM line plane on the MRI, the centers of both external acoustic meatuses and the centers of both eyes are detected, and the plane containing these serve as an approximate OM line plane.

FIG. 4 is a cross-sectional view of a brain scanned parallelly to the OM line. FIG. 4 (a) is an image according to slice plane S5, FIG. 4 (b) is an image according to slice plane S6, FIG. 4 (c) is an image according to slice plane S7, FIG. 4 (d) is an image according to slice plane S8, FIG. 4 (e) is an image according to slice plane S9 and FIG. 4 (f) is an image according to slice plane S10. The black portions and the vertically hatched portions in the periphery are grey matter 13, and the white portions in the interior thereof are white matter 15. A cranial bone 14 is present on the outer side of the grey matter; however, in some places, cerebrospinal fluid 11 cavities are seen between the cranial bone and the grey matter. Reference numeral 12 is a cerebral ventricle filled with cerebrospinal fluid.

The concept of a two-dimensional convex hull is shown in FIG. 5. A curve 20 on the outside indicates a convex hull and a curve 21 is a given diagram. A convex hull is a convex diagram that internalizes a given diagram with the minimum surface area.

Since the present invention allows multiple numerical values to be collected objectively regarding the extent of the atrophy of a brain, by taking the correspondence relationship between this numerical value and various conditions thought to be caused by cerebral atrophy, the status of the progression of a condition can be converted into numbers, allowing for a prediction/assessment of the state of cerebral atrophy, such as an assessment of the necessity for a treatment or the timing for starting a treatment.

In addition, since conversion into data regarding a multitude of samples is possible, objectivity is obtained in the assessment of cerebral atrophy.

The invention claimed is:

1. A cerebral atrophy assessment device, comprising:
acquisition means for acquiring a slice image of a head portion, said acquisition means comprising a nuclear magnetic resonance imaging (MRI) device;
volume calculation means for calculating a numerical value representing a volume of a tissue or a region in said head portion based on intensities of pixels constituting the slice image acquired by said acquisition means;
assessment means for assessing cerebral atrophy in said head portion from one or more numerical values calculated by said volume calculation means on a basis of preset assessment criteria;
and output means for outputting information indicating an assessment result according to said assessment means;
wherein said volume calculation means calculates a numerical value representing a brain volume comprising at least one of a volume of grey matter and a volume of white matter of said head portion, and based on the intensities of pixels constituting said slice image acquired by said acquisition means, calculates a shape of at least one of the grey matter and the white matter of said head portion, and calculates a convex hull of said shape to calculate a numerical value representing a volume of said convex hull, and said assessment means calculates a value of a first ratio between the numerical value representing the volume of said convex hull and the numerical value representing said brain volume and assesses said cerebral atrophy from the value of said first ratio.

2. The cerebral atrophy assessment device according to claim 1, wherein said acquisition means acquires a plurality of said slice images, and said volume calculation means calculates each numerical value based on said plurality of said slice images.

3. The cerebral atrophy assessment device according to claim 1, wherein said volume calculation means calculates a numerical value representing an intracranial volume of said head portion and said assessment means calculates a value of a second ratio between the numerical value representing the intracranial volume of said head portion and the numerical value representing said brain volume calculated by said volume calculation means and assesses said cerebral atrophy from the value of said second ratio.

4. The cerebral atrophy assessment device according to claim 3, wherein said volume calculation means separates an outer portion of a brain and a cerebral ventricle portion within said intracranial volume and calculates a numerical value representing a volume of cerebrospinal fluid of a region occupied by the cerebrospinal fluid, and said assessment means assesses said cerebral atrophy based also on the numerical value representing said volume of cerebrospinal fluid calculated by said volume calculation means.

5. The cerebral atrophy assessment device according to claim 1, wherein said volume calculation means, based on the intensities of pixels constituting said slice image, distinguishes, by way of an Expectation-Maximization (EM) algorithm, the tissue or the region of said head portion indicated by said pixels, and calculates the numerical value representing said volume of the tissue or the region in said head portion.

6. The cerebral atrophy assessment device according to claim 5, wherein said volume calculation means calculates, by way of said EM algorithm, a probability that said pixels indicate the tissue or the region of said head portion, and calculates the value representing said volume of the tissue or the region in said head portion based on the calculated probability.

7. The cerebral atrophy assessment device according to claim 1, wherein said slice image is a slice image obtained by MRI.

8. The cerebral atrophy assessment device according to claim 1, wherein said slice image is an image of a cross-section in a plane that is parallel to a plane passing through centers of external acoustic meatuses and centers of the eyes in said head portion.

9. A cerebral atrophy assessment method, performed by an information processing device, the method comprising the steps of:
    acquiring a slice image of a head portion using an acquisition means for acquiring said slice image of said head portion, said acquisition means comprising a nuclear magnetic resonance imaging (MRI) device;
    calculating a numerical value representing a volume of a tissue or a region in said head portion using a volume calculation means for calculating said numerical value representing said volume of said tissue or said region in said head portion based on intensities of pixels constituting said slice image acquired in said acquiring step;
    calculating a numerical value representing a brain volume comprising at least one of a volume of grey matter and a volume of white matter of said head portion using said volume calculation means;
    calculating a shape using of at least one of the grey matter and the white matter of said head portion based on the intensities of pixels constituting said slice image acquired in said acquiring step using said volume calculation means;
    calculating a convex hull of said shape and calculating a numerical value representing a volume of said convex hull using said volume calculation means:
    calculating a value of a ratio between the numerical value representing the volume of said convex hull and the numerical value representing said brain volume using an assessment means for assessing cerebral atrophy in said head portion from one or more numerical values calculated by said volume calculation means on a basis of preset assessment criteria;
    assessing cerebral atrophy in said head portion from the value of said ratio using said assessment means; and
    outputting information indicating an assessment result of said assessing step using an output means for indicating the assessment result according to said assessment means.

10. A non-transitory computer readable medium on which stores a cerebral atrophy assessment program causing an information processing device to execute:
    an acquisition function for acquiring a slice image of a head portion using an acquisition means for acquiring said slice image of said head portion, said acquisition means comprising a nuclear magnetic resonance imaging (MRI) device;
    a first volume calculation function for calculating a numerical value representing a volume of a tissue or a region in said head portion using a volume calculation means for calculating said numerical value representing said volume of said tissue or said region in said head portion based on intensities of pixels constituting said slice image acquired by said acquisition function;
    a second volume calculation function for calculating a numerical value representing a brain volume comprising at least one of a volume of grey matter and a volume of white matter of said head portion using said volume calculation means;
    a shape calculation function for calculating a shape of at least one of the grey matter and the white matter of said head portion based on the intensities of pixels constituting said slice image acquired by said acquisition function using said volume calculation means;
    a calculation function for calculating a convex hull of said shape and calculating a numerical value representing a volume of said convex hull using said volume calculation means;
    a ratio calculation function for calculating a value of a ratio between the numerical value representing the volume of said convex hull and the numerical value representing said brain volume using an assessment means for assessing cerebral atrophy in said head portion from one or more numerical values calculated by said volume calculation means on a basis of preset assessment criteria;
    an assessment function for assessing cerebral atrophy in said head portion from the value of said ratio using said assessment means;
    and an output function for outputting information indicating an assessment result according to said assessment function using an output means for indicating an assessment result according to said assessment means.

* * * * *